US011974950B2

(12) United States Patent
Berlin

(10) Patent No.: US 11,974,950 B2
(45) Date of Patent: *May 7, 2024

(54) METHODS AND SYSTEMS FOR THE TREATMENT OF GLAUCOMA USING VISIBLE AND INFRARED ULTRASHORT LASER PULSES

(71) Applicant: Michael S. Berlin, Las Vegas, NV (US)

(72) Inventor: Michael S. Berlin, Las Vegas, NV (US)

(*) Notice: Subject to any disclaimer, the term of this patent is extended or adjusted under 35 U.S.C. 154(b) by 0 days.

This patent is subject to a terminal disclaimer.

(21) Appl. No.: 18/356,590

(22) Filed: Jul. 21, 2023

(65) Prior Publication Data
US 2023/0355442 A1 Nov. 9, 2023

Related U.S. Application Data

(63) Continuation of application No. 18/045,229, filed on Oct. 10, 2022, now Pat. No. 11,857,463, which is a (Continued)

(51) Int. Cl.
*A61F 9/008* (2006.01)
*A61F 9/009* (2006.01)

(52) U.S. Cl.
CPC .......... *A61F 9/00825* (2013.01); *A61F 9/009* (2013.01); *A61F 9/0084* (2013.01); (Continued)

(58) Field of Classification Search
CPC .............. A61F 9/00802; A61F 9/00814; A61F 9/00825; A61F 9/084; A61F 2009/00851; (Continued)

(56) References Cited

U.S. PATENT DOCUMENTS 3,858,577 A 1/1975 Bass
3,884,236 A 5/1975 Krasnov
(Continued)

FOREIGN PATENT DOCUMENTS

DE 19840047 A1 3/2000
EP 0898947 A2 3/1999
(Continued)

OTHER PUBLICATIONS

Owen, David. A moving-mirror gonioscope for retinal surgery. 1997. British Journal of Ophthalmology, 61, 246-247.
(Continued)

*Primary Examiner* — Ahmed M Farah
(74) *Attorney, Agent, or Firm* — FISHERBROYLES, LLP; John K. Shimmick

(57) ABSTRACT

Transcorneal and fiberoptic laser delivery systems and methods for the treatment of eye diseases wherein energy is delivered by wavelengths transparent to the cornea to effect target tissues in the eye for the control of intraocular pressure in diseases such as glaucoma by delivery systems both external to and within ocular tissues. External delivery may be affected under gonioscopic control. Internal delivery may be controlled endoscopically or fiberoptically, both systems utilizing femtosecond laser energy to excise ocular tissue. The femtosecond light energy is delivered to the target tissues to be treated to effect precisely controlled photodisruption to enable portals for the outflow of aqueous fluid in the case of glaucoma in a manner which minimizes target tissue healing responses, inflammation and scarring.

9 Claims, 7 Drawing Sheets

Related U.S. Application Data continuation of application No. 17/302,965, filed on May 17, 2021, now Pat. No. 11,510,813, which is a continuation of application No. 16/881,934, filed on May 22, 2020, now Pat. No. 11,039,958, which is a continuation of application No. 16/008,917, filed on Jun. 14, 2018, now Pat. No. 10,765,559, which is a continuation of application No. 14/732,627, filed on Jun. 5, 2015, now Pat. No. 10,064,757, which is a continuation of application No. 13/464,949, filed on May 4, 2012, now abandoned.

(60) Provisional application No. 61/482,824, filed on May 5, 2011.

(52) U.S. Cl.
CPC ............... *A61F 2009/00851* (2013.01); *A61F 2009/00865* (2013.01); *A61F 2009/00868* (2013.01); *A61F 2009/00891* (2013.01); *A61F 2009/00897* (2013.01)

(58) Field of Classification Search
CPC .. A61F 2009/00868; A61F 2009/00891; A61F 2009/00897
USPC .......................................................... 606/3, 6
See application file for complete search history.

(56) References Cited

U.S. PATENT DOCUMENTS

| | | |
|---|---|---|
| 3,982,541 A | 9/1976 | L'Esperance, Jr. |
| 4,273,109 A | 6/1981 | Enderby |
| 4,391,275 A | 7/1983 | Fankhauser |
| 4,461,294 A | 7/1984 | Baron |
| 4,470,407 A | 9/1984 | Hussein |
| 4,497,319 A | 2/1985 | Sekine |
| 4,501,274 A | 2/1985 | Skjaerpe |
| 4,517,973 A | 5/1985 | Sunago |
| 4,538,608 A | 9/1985 | L'Esperance, Jr. |
| 4,551,129 A | 11/1985 | Coleman |
| 4,558,698 A | 12/1985 | O'Dell |
| 4,559,942 A | 12/1985 | Eisenberg |
| 4,580,559 A | 4/1986 | L'Esperance |
| 4,583,539 A | 4/1986 | Karlin |
| 4,633,866 A | 1/1987 | Peyman |
| 4,658,816 A | 4/1987 | Ector, Jr. |
| 4,660,546 A | 4/1987 | Herrick |
| 4,671,273 A | 6/1987 | Lindsey |
| 4,722,350 A | 2/1988 | Armeniades |
| 4,729,373 A | 3/1988 | Peyman |
| 4,770,654 A | 9/1988 | Rogers |
| 4,791,927 A | 12/1988 | Menger |
| 4,846,172 A | 7/1989 | Berlin |
| 4,876,250 A | 10/1989 | Clark |
| 4,925,299 A | 5/1990 | Meisberger |
| 4,994,060 A | 2/1991 | Rink |
| 5,034,010 A | 7/1991 | Kittrell |
| 5,092,837 A | 3/1992 | Ritch |
| 5,123,902 A | 6/1992 | Mueller |
| 5,129,895 A | 7/1992 | Vassiliadis |
| 5,254,112 A | 10/1993 | Sinofsky |
| 5,273,056 A | 12/1993 | McLaughlin |
| 5,300,020 A | 4/1994 | L'Esperance, Jr. |
| 5,359,685 A | 10/1994 | Waynant |
| 5,360,399 A | 11/1994 | Stegmann |
| 5,371,078 A | 12/1994 | Clark |
| 5,607,966 A | 3/1997 | Hellberg |
| 5,643,250 A | 7/1997 | O'Donnell, Jr. |
| 5,657,760 A | 8/1997 | Ying |
| 5,698,545 A | 12/1997 | Clark |
| 5,704,907 A | 1/1998 | Nordquist |
| 5,713,844 A | 2/1998 | Peyman |
| 5,722,970 A | 3/1998 | Colvard |
| 5,736,491 A | 4/1998 | Patel |
| 5,738,676 A | 4/1998 | Hammer |
| 5,738,677 A | 4/1998 | Colvard |
| 5,785,658 A | 7/1998 | Benaron |
| 5,792,103 A | 8/1998 | Schwartz |
| 5,811,453 A | 9/1998 | Yanni |
| 5,865,831 A | 2/1999 | Cozean |
| 5,885,279 A | 3/1999 | Bretton |
| 5,895,831 A | 4/1999 | Brasier |
| 5,990,099 A | 11/1999 | Clark |
| 5,993,438 A | 11/1999 | Juhasz |
| 5,997,531 A | 12/1999 | Loeb |
| 6,002,480 A | 12/1999 | Izatt |
| 6,059,772 A | 5/2000 | Hsia |
| 6,083,193 A | 7/2000 | Kadziauskas |
| 6,099,521 A | 8/2000 | Shadduck |
| 6,102,045 A | 8/2000 | Nordquist |
| 6,146,375 A | 11/2000 | Juhasz |
| 6,177,544 B1 | 1/2001 | Kanai |
| 6,186,974 B1 | 2/2001 | Allan |
| 6,251,103 B1 | 6/2001 | Berlin |
| 6,297,228 B1 | 10/2001 | Clark |
| 6,398,809 B1 | 6/2002 | Hoffmann |
| 6,450,984 B1 | 9/2002 | Lynch |
| 6,494,857 B1 | 12/2002 | Neuhann |
| 6,524,275 B1 | 2/2003 | Lynch |
| 6,638,239 B1 | 10/2003 | Bergheim |
| 7,018,376 B2 | 3/2006 | Webb |
| 7,125,119 B2 | 10/2006 | Farberov |
| 7,133,137 B2 | 11/2006 | Shimmick |
| 7,331,984 B2 | 2/2008 | Tu |
| 7,431,710 B2 | 10/2008 | Tu |
| 7,503,916 B2 | 3/2009 | Shimmick |
| 8,123,729 B2 | 2/2012 | Yamamoto |
| 8,540,659 B2 | 9/2013 | Berlin |
| 8,679,089 B2 * | 3/2014 | Berlin ................... A61F 9/0017 604/521 |
| 9,033,963 B2 * | 5/2015 | Vera ................... A61F 9/00825 606/4 |
| 9,820,883 B2 | 11/2017 | Berlin |
| 10,064,757 B2 * | 9/2018 | Berlin ................. A61F 9/00825 |
| 10,383,689 B2 | 8/2019 | Berlin |
| 10,765,559 B2 * | 9/2020 | Berlin ................. A61F 9/00825 |
| 11,039,958 B2 * | 6/2021 | Berlin ................. A61F 9/00825 |
| 11,510,813 B2 * | 11/2022 | Berlin ................. A61F 9/009 |
| 11,857,463 B2 * | 1/2024 | Berlin ................. A61F 9/00825 |
| 2002/0013572 A1 | 1/2002 | Berlin |
| 2002/0072673 A1 | 6/2002 | Yamamoto |
| 2002/0082591 A1 | 6/2002 | Haefliger |
| 2002/0111608 A1 | 8/2002 | Baerveldt |
| 2002/0133168 A1 | 9/2002 | Smedley |
| 2002/0165522 A1 | 11/2002 | Holmen |
| 2003/0014092 A1 | 1/2003 | Neuhann |
| 2003/0105456 A1 | 6/2003 | Lin |
| 2003/0109907 A1 | 6/2003 | Shadduck |
| 2003/0175324 A1 | 9/2003 | Robinson |
| 2003/0212387 A1 | 11/2003 | Kurtz |
| 2003/0236483 A1 | 12/2003 | Ren |
| 2004/0070761 A1 | 4/2004 | Horvath |
| 2004/0082939 A1 | 4/2004 | Berlin |
| 2004/0092856 A1 | 5/2004 | Dahan |
| 2004/0102729 A1 | 5/2004 | Haffner |
| 2004/0116909 A1 | 6/2004 | Neuberger |
| 2004/0199149 A1 | 10/2004 | Myers |
| 2004/0216749 A1 | 11/2004 | Tu |
| 2004/0228013 A1 | 11/2004 | Goldstein |
| 2005/0043722 A1 | 2/2005 | Lin |
| 2005/0165386 A1 | 7/2005 | Kurtz |
| 2005/0240168 A1 | 10/2005 | Neuberger |
| 2005/0245916 A1 | 11/2005 | Connor |
| 2005/0279369 A1 | 12/2005 | Lin |
| 2006/0021623 A1 | 2/2006 | Miller |
| 2006/0050229 A1 | 3/2006 | Farberov |
| 2006/0084954 A1 | 4/2006 | Zadoyan |
| 2006/0106370 A1 | 5/2006 | Baerveldt |
| 2006/0114469 A1 | 6/2006 | Horvath |
| 2006/0129141 A1 | 6/2006 | Lin |
| 2006/0155265 A1 | 7/2006 | Juhasz |
| 2006/0195078 A1 | 8/2006 | Webb |

(56) References Cited

U.S. PATENT DOCUMENTS

| | | |
|---|---|---|
| 2006/0200113 A1 | 9/2006 | Haffner |
| 2006/0224146 A1 | 10/2006 | Lin |
| 2006/0259021 A1 | 11/2006 | Lin |
| 2007/0093794 A1 | 4/2007 | Wang |
| 2007/0093796 A1 | 4/2007 | Raksi |
| 2007/0121120 A1 | 5/2007 | Schachar |
| 2007/0173791 A1 | 7/2007 | Raksi |
| 2007/0208325 A1 | 9/2007 | Kurtz |
| 2007/0219541 A1 | 9/2007 | Kurtz |
| 2007/0235543 A1 | 10/2007 | Zadoyan |
| 2007/0236771 A1 | 10/2007 | Zadoyan |
| 2008/0027519 A1 | 1/2008 | Guerrero |
| 2008/0058777 A1 | 3/2008 | Kurtz |
| 2008/0082078 A1 | 4/2008 | Berlin |
| 2008/0082088 A1 | 4/2008 | Kurtz |
| 2008/0091224 A1 | 4/2008 | Griffis, III |
| 2008/0119827 A1 | 5/2008 | Kurtz |
| 2008/0278687 A1 | 11/2008 | Somani |
| 2009/0118716 A1 | 5/2009 | Brownell |
| 2009/0118717 A1 | 5/2009 | Brownell |
| 2009/0118718 A1 | 5/2009 | Raksi |
| 2009/0131921 A1 | 5/2009 | Kurtz |
| 2009/0137988 A1 | 5/2009 | Kurtz |
| 2009/0157062 A1 | 6/2009 | Hauger |
| 2009/0171327 A1 | 7/2009 | Kurtz |
| 2009/0281530 A1 | 11/2009 | Korn |
| 2010/0036488 A1 | 2/2010 | De Juan, Jr. |
| 2010/0324543 A1 | 12/2010 | Kurtz |
| 2011/0028948 A1 | 2/2011 | Raksi |
| 2011/0028949 A1 | 2/2011 | Raksi |
| 2011/0028950 A1 | 2/2011 | Raksi |
| 2011/0028951 A1 | 2/2011 | Raksi |
| 2011/0028952 A1 | 2/2011 | Raksi |
| 2011/0028953 A1 | 2/2011 | Raksi |
| 2011/0028954 A1 | 2/2011 | Raksi |
| 2011/0028955 A1 | 2/2011 | Raksi |
| 2011/0028957 A1 | 2/2011 | Raksi |
| 2011/0028958 A1 | 2/2011 | Raksi |
| 2012/0259321 A1* | 10/2012 | Vera ............... A61F 9/00781 606/6 |
| 2012/0283557 A1 | 11/2012 | Berlin |
| 2013/0103011 A1 | 4/2013 | Grant |
| 2014/0288485 A1 | 9/2014 | Berlin |
| 2015/0080783 A1 | 3/2015 | Berlin |
| 2015/0305939 A1 | 10/2015 | Vera |
| 2015/0305940 A1 | 10/2015 | Vera |
| 2015/0313759 A1 | 11/2015 | Vera |
| 2016/0262606 A1 | 9/2016 | Mosaed |

FOREIGN PATENT DOCUMENTS

| | | |
|---|---|---|
| JP | 2017099757 | 6/2017 |
| WO | 9117793 A1 | 11/1991 |
| WO | 9620742 A1 | 7/1996 |
| WO | 9901063 A1 | 1/1999 |
| WO | 9945868 A1 | 9/1999 |
| WO | 0013627 A1 | 3/2000 |
| WO | 0067687 | 11/2000 |
| WO | 2017094243 | 6/2017 |

OTHER PUBLICATIONS

Berlin, et al., Excimer laser photoablation in glaucoma filtering surgery. American journal of ophthalmology, 103.5 (1987):713.
Berlin, et al. Goniophotoablation: excimer laser glaucoma filtering surgery. Lasers Light Ophthalmol 2 (1988): 17-24.
Berlin, et al. Laser sclerostomy. The state of the art. Ophthalmol Clin North Am 6 (1993): 415-424.
Berlin, et al. Perspectives on new laser techniques in managing glaucoma. Ophthalmol Clin North Am 8 (1995): 341-363.
Berlin, M. Laser Therapy. In Becker-Shaffer's Diagnosis and Therapy of the Glaucomas. 1999:521-554.
Berlin M.D., M., "Photoablation—The Basis of Photochemical Laser Interactions," Ophthalmic Lasers: A Second Generation, Edited by W. Mar. M.D., 1990, pp. 85-91.
Berson, M.D., F.G., et al. "Obstruction of Aqueous Outflow by Sodium Hyaluronate in Enucleanted Human Eyes", American Journal of Ophthalmology, vol. 95, No. 5, 1983, pp. 668-672.
Brown M.D., R.H., et al. "Ab Interne Filtering Surgery Internal Sclerectomy with the Trabecuphine," Ophthalmology Clinics of North America, vol. 1, No. 2, Dec. 1988, pp. 199-207.
Cimberle, M. "Erbium Laser Cataract Surgery is Now Bimanual, Easier and Safer to Perform" Ocular Surgery News, Aug. 2000, 3 pages.
"Customized Ablation: The Wave Continues to Move Forward", Medical Laser Report, vol. 15, No. 12, Dec. 2001, pp. 4-5.
Dietlein, et al. Ab interno infrared laser trabecular ablation: preliminary short-term results in patients with open-angle glaucoma. Graefe's archive for clinical and experimental ophthalmology 235.6 (1997): 349-353.
Dietlein, et al. Erbium: YAG laser trabecular ablation (LTA) in the surgical treatment of glaucoma. Lasers in surgery and medicine 23.2 (1998): 104-110.
Dietlein et al; "Erbium:YAG Laser Ablation on Human Trabecular Meshwork by Contact Delivery Endoprobes"; Ophthalmic Surgery and Lasers; vol. 27, No. 11; Nov. 1996; pp. 939-945.
Dietlein, et al. Morphological variability of the trabecular meshwork in glaucoma patients: implications for non-perforating glaucoma surgery. British journal of ophthalmology 84.12 (2000): 1354-1359.
L'Esperance. Jr. M.D. "Ophthalmic Lasers Photocoagulation, Photoradiation and Surgery," The C.V. Mosby Company, 1983, pp. 529-554.
Fankhauser, et al. Optical principles related to optimizing sclerostomy procedures. Ophthalmic Surgery, Lasers and Imaging Retina 23(11): 752-761 (1992).
Hill, et al. Effects of pulse width on erbium: YAG laser photothermal trabecular ablation (LTA). Lasers in surgery and medicine 13.4 (1993): 440-446.
Hill, et al. Laser trabecular ablation (LTA). Lasers in surgery and medicine 11.4 (1991): 341-346.
Huang, et al. Optical coherence tomography. Science (New York, NY) 254.5035 (1991):1178-1181.
Iliev, et al. The repair response following Nd: YAG laser sclerostomy ab interno in rabbits. Experimental eye research 61.3 (1995):311-321.
International preliminary examination report dated Sep. 19, 2002 for PCT Application No. PCT/US01/16317.
International search report dated Jul. 5, 2002 for PCT Application No. PCT/US01/16317.
Jacobi, et al. Microendoscopic trabecular surgery in glaucoma management. Ophthalmology 106.3 (1999): 538-544.
Juhasz, et al. Application of Femtosecond Laser Surgery for the Treatment of Glaucoma; in Frontiers in Optics. OSA Technical Digest (CD) (Optical Society of America, 2008).
Larson M.D. et al., "Viscoelastic Agents", The CLAO Journal, vol. 15, No. 2, Apr. 1989, 10 pages.
Latina, et al. New Lasers for Glaucoma Surgery. In Principles and Practice of Ophthalmology. Elsevier Health Sciences. 2000:600-608.
Lee, et al. Short-pulsed neodymium-YAG laser trabeculotomy. An in vivo morphological study in the human eye. Investigative ophthalmology & visual science 29.11 (1988):1698-1707.
Leitgeb, et al. Spectral measurement of absorption by spectroscopic frequency-domain optical coherence tomography. Optics letters 25.11 (2000):820-822.
Liesegang M.D., T., Viscoelastics, Interactions Opthalmology Clinics, vol. 33, No. 4, 1993, pp. 127-147.
Lin, C. Ph.D. Laser-Tissue Interactions. Ophthalmology Clinics of North America, vol. 6, No. 3, Sep. 1993, pp. 381-391.
M. Vogel, G. Scheurer, W. Neu, M. Dressel, H. Gerhardt, "Die Ablation des Trabekelwerks," Klin. Mbl. Augenheilk. 197 (1990) 250-253.
Martin Vogel, Kyra Lauritzen, "Punktuelle Excimerlaserablation des Trabekelwers Klinische Ergebnisse," Opthalmologe 1997 94:665-667.

(56) References Cited

OTHER PUBLICATIONS

M.Berlin M.D., "Coreneal Photoblation,"Ophthalmic Lasers: A second Generation, Edited by March . M.d., 1990, pp. 93-104.

M.Berlin M.D., Excimer Laser Applications in Glaucona Surgery, Ophthalmology Clinics of North America, vol. 1, No. 2. Dec. 1988, pp. 255-263.

McHam, et al. Erbium: YAG laser trabecular ablation with a sapphire optical fiber. Experimental eye research 65.2 (1997): 151-155.

M.H. Vogel, P. Schildberg, "Histologische Friihergebnisse nach experimenteller Lasertrabekulopunktur," Klin. Mhl. Augenheilk. 163 (1973) 353-358.

Muller, et al. Biophysics of the photoablation process. Lasers in Medical Science 6.3 (1991): 241-254.

Nakamura, et al. Femtosecond laser photodisruption of primate trabecular meshwork: an ex vivo study. Invest Ophthalmol Vis Sci. Mar. 2009; 50(3):1198-204. doi: 10.1167/iovs.07-1536. Epub Oct. 3, 2008.

Neuhann, et al., "Excimer Laser Trabecular Ablation ab interne (EL T) in the Treatment of Chronic Open-Angle Glaucoma", Ophthalmo-Chirurgie 13:Offprint (2001).

Olivius M.D., E., et al., "Interocular Pressure After Cataract Surgery with Healon," American Intraocular Implant Society, vol. 11, Sep. 1985, pp. 480-482.

Royston, et al. Comparison of the thermal tissue effects produced by aged sapphire and silica hemispherical tips. Lasers in surgery and medicine 14.1 (1994):47-58.

Taboada, J. et al., "An Extreme Sensitivity in the Corneal Epithelium to FAR UV ArF Excimer Laser Pulses," Proc. of the Sci. Prog. of the Aerospace Med. Assoc., 1981, San Antonio, TX. pp. 98-99.

Toyran, et al., Femtosecond laser photodisruption of human trabecular meshwork: an in vitro study. Exp Eye Res., Sep. 2005; 81(3):298-305.

Translated Article: Punktuelfe Excimerlaserablation des Trabekelwerks Klinische Ergebnisse (Punctual Excimer Laser Ablation of trabecular meshwork Clinical results) by Lauritzen and Vogel; Opthalmologe 1997 94:665-667.

Translated Article: "Showing translation for The ablation of the trabecular meshwork . . . " M. Vogel, G. Scheurer, W Neu, M. Dressel, H. Gerhardt; Klin. Mbl. Augenheilk. 197 (1990) 250-253.

Translated Article of M.H. Vogel, P. Schildberg, "[Histological findings after experimental laser-trabecula-puncture (author's transl)]," Klin. Monbl Augenheilkd 1973, 163(3):353-358.

Trokel M.D., S. et al., "Excimer Laser Surgery of the Cornea," American Journal of Ophthalmology, vol. 96, Dec. 1983, pp. 710-715.

Verdaasdonk, R.M., et al., "Ray Tracing of Optically Modified Fiber Tips 1: Spherical Probes," Applied Optics, vol. 30, No. 16, Jun. 1991, pp. 2159-2171.

Verdaasdonk, R.M., et al., "Ray Tracing of Optically Modified Fiber Tips 2: Laser Scalpels" Applied Optics, vol. 30, No. 16, Jun. 1991, pp. 2172-2177.

Wolbarsht, M., "Laser Surgery: C02 or HF," Journal of Quantum Electronics, vol. QE20, No. 12, Dec. 1984, pp. 1427-1432.

Shirato et al., "Internal Sclerostomy with Argon Contact Laser—Animal Experiment Using 5-Fluorouracil", Japanese Journal of Opthalmol, 34(3); 1990; 381-387.

M. Berlin M.D., "New Developments in Glaucoma Laser Surgery Procedures," Ophthalmology clinics of North America. vol. 11. No. 2. Jun. 1998, pp. 187-200.

Jean et al. "Noncontact photoacoustic spectroscopy during photoablation with a 193-nm excimer laser", Ger. J. Ophthalmol.; vol. 2, No. 6; Nov. 1993; pp. 404-408.

* cited by examiner

METHODS AND SYSTEMS FOR THE TREATMENT OF GLAUCOMA USING VISIBLE AND INFRARED ULTRASHORT LASER PULSES

RELATED APPLICATIONS

This application is a continuation of U.S. patent application Ser. No. 18/045,229, filed Oct. 10, 2022, now U.S. Pat. No. 11,857,463, issued Jan. 2, 2024, which is a continuation of U.S. patent application Ser. No. 17/302,965, filed May 17, 2021, now U.S. Pat. No. 11,510,813, issued Nov. 29, 2022, which is a continuation of U.S. patent application Ser. No. 16/881,934, filed May 22, 2020, now U.S. Pat. No. 11,039,958, issued Jun. 22, 2021, which is a continuation of U.S. patent application Ser. No. 16/008,917, filed Jun. 14, 2018, now U.S. Pat. No. 10,765,559, issued Sep. 8, 2020, which is a continuation of U.S. patent application Ser. No. 14/732,627, filed Jun. 5, 2015, now U.S. Pat. No. 10,064,757, issued Sep. 4, 2018, which is a continuation of U.S. patent application Ser. No. 13/464,949, filed May 4, 2012, abandoned, which claims the benefit under 35 U.S.C. § 119(e) of U.S. Provisional Application No. 61/482,824, filed May 5, 2011, each of which are hereby incorporated by reference in their entireties.

BACKGROUND

Field of the Invention

The present invention pertains generally to methods and procedures for use in ophthalmic surgery. More particularly, the present invention pertains to the use of laser devises for photodisruption of tissue in the eye. The present invention is particularly, but not exclusively, useful for an ophthalmic surgical procedure involving transcorneal or fiberoptic photodisruption of tissue of the corneo scleral angle as a treatment for glaucoma.

Background of the Invention

Glaucoma refers to a series of relatively common eye disorders in which pressure within the eye is sufficiently high as to result in damage to sensitive intraocular structures, including the retina and optic nerve. Glaucomas are classified as primary (including chronic open angle glaucoma, angle closure glaucoma, mixed mechanism glaucoma and infantile glaucoma and secondary (related to other diseases of the eye). The elevation of intraocular pressure ultimately leads to irreversible destruction of the optic nerve. The clinical symptoms, which are not readily recognized in the early stages, are characterized mainly by a slow, relentless, progressive narrowing of the field of vision, and decrement in visual integration processing, including diminished dark adaptation. In the absence of treatment, the eventual outcome is total loss of vision often accompanied by severe eye pain.

In order to fully appreciate the described embodiments, a brief overview of the anatomy of the eye is provided. As schematically shown in FIG. 1, the outer layer of the eye includes a sclera 17 that serves as a supporting framework for the eye. The front of the sclera includes a cornea 15, a transparent tissue that enables light to enter the eye. An anterior chamber 7 is located between the cornea 15 and the crystalline lens 4. The anterior chamber 7 contains a constantly flowing clear fluid called aqueous humor 1. The crystalline lens 4 is connected to the eye by fiber zonules, which are connected to the cilliary body 3. In the anterior chamber 7, an iris 19 encircles the outer perimeter of the lens 4 and includes a pupil 5 at its center. The diameter of the pupil 5 controls the amount of light passing through the lens 4 to the retina 8. A posterior chamber 2 is located between the crystalline lens 4 and the retina 8.

As shown in FIG. 2, the anatomy of the eye also includes a trabecular meshwork 9, a narrow band of spongy tissue within the eye that encircles the iris 19. The trabecular meshwork ("TM") varies in shape and is microscopic in size. It is generally triangular in cross-section, varying in thickness from about 100 μm to 200 μm. It is made up of different fibrous layers, having micro-sized pores forming fluid pathways for the egress of aqueous humor from the anterior chamber. The trabecular meshwork 9 has been measured to a thickness of about 100 μm at its anterior edge, Schwalbe's line, 18 at the approximate juncture of cornea 15 and sclera 17.

The trabecular meshwork widens to about 200 μm at its base where it and the iris 19 attach to the scleral spur. The passageway through the pores in the trabecular meshwork 9 lead through a very thin, porous tissue called the juxtacanalicular trabecular meshwork 13, which in turn abuts the interior side of a structure called Schlemm's canal 11. Schlemm's canal 11 is filled with a mixture of aqueous humor and blood components and branches off into collector channels 12 that drain the aqueous humor into the venous system. Because aqueous humor is continuously produced by the eye, any obstruction in the trabecular meshwork, the juxtacanalicular trabecular meshwork or Schlemm's canal, prevents the aqueous humor from readily escaping from the anterior chamber. This results in an elevation of intraocular pressure in the eye. Increased intraocular pressure can lead to damage of the optic nerve and eventual blindness.

Present surgical techniques to lower intraocular pressure include procedures enabling fluid to drain from within the eye to extra ocular sites. However, these drainage or "filtering" procedures not only increase the risk of causing a lens cataract, but often fail by virtue of their closure resulting from the healing of the very wound created for gaining access to the surgical site. Ab inferno surgical procedures, also, if not adequately stealth eventually fail. In creating the egress by photoablation or by photodisruption less inflammation at the egress site is induced than by current techniques, thus prolonging filtration wound function.

Lasers were first used in 1965 to repair retinal detachments. The procedure involved chorioretinal coagulation in which a laser beam positioned from without the eye was used to achieve fusion of the retina and the choroid. The technique consisted of introducing a laser beam from outside the cornea, and by employing the refractive media of the eye itself, the laser radiation was directed in such a manner that it was concentrated at a selected point upon the retina/choroid so that the tissues in a very localized area were photothermally congealed.

In contrast to thermal energy produced by visible and by infrared lasers, such as Nd:YAG systems, the high photon energies of femtosecond lasers can photodisrupt the material in question, namely eye tissue, in a manner which does not cause significant target tissue temperature elevation. By photodisruption, both visible and infrared femtosecond laser radiation can be used to drastically alter the target tissue in a "cold" environment. This becomes significant for controlled removal of organic substances, such as living tissue, in contradistinction to treatments in which heat is generated, e.g. by thermal lasers, which could damage, if not destroy, delicate eye tissue adjacent to the target sites to be removed and thereby induce healing responses.

Femtosecond ("FS") lasers used for this purpose include the group of rapidly pulsed lasers which emit at 0.4 to 2.5 μm in the visible and infrared spectra. In contrast to the thermal visible and infrared radiation from some Nd:YAG or $CO_2$ lasers or the like, the high energy photons from femtosecond lasers at photodisruptive fluence levels are absorbed by the target tissues. This absorption creates a hot plasma at the focus, vaporizing tissue. The plasma subsequently expands supersonically launching a pressure wave. Later, a cavitation bubble forms and eventually collapses. The extent of the tissue damage caused by the pressure wave and cavitation bubble expansion is energy-dependent. Femtosecond pulses deposit very little energy while still causing breakdown, therefore producing surgical photodisruption while minimizing collateral damage.

Juhasz T, Chai D, Chaudhary G, et al.; Application of Femtosecond Laser Surgery for the Treatment of Glaucoma; in Frontiers in Optics, OSA Technical Digest (CD) (Optical Society of America, 2008) disclosed that FS laser pulses could be used to create partial thickness scleral channels that drain aqueous humor into the sub-conjunctival space, showing potential for the treatment of glaucoma. Toyran S, Liu Y, Singha S., et al.

Femtosecond laser photodisruption of human trabecular meshwork: an in vitro study; Exp. Eye Res. 2005; 81(3); 298-305, disclosed the use of FS lasers to perform photodisruption of human TM strips ex vivo, creating full-thickness ablation channels through the TM without collateral damage. The ideal settings for creating lesions with minimal collateral side effects on the inner surface of the TM are: Ti:Sapphire laser beam (45 fsec, 1 kHz, 800 nm) with 14.4 mJ pulse energy and an exposure time of 0.5 sec Nakamura H, Liu Y, Witt T E, et al.; Femtosecond laser photodisruption of primate trabecular meshwork: an ex vivo study; Invest. Ophthalmol. Vis. Sci. 2009; 1198-204 disclosed photodisruption by FS laser of the TM of ex vivo, intact, enucleated human and baboon eyes. The settings were 45 fsec, 1 kHz, 800 nm with 60 to 480 μJ and 0.001 to 0.3 sec exposure time. The study showed that laser ablation of the TM ab interno in ex vivo primate eyes is feasible by a custom femtosecond laser ablation system with a gonioscopic lens. The photodisruption did not reach Schlemm's canal, although this goal could easily be achieved through an alteration in laser settings and delivery methods.

However, successful use of ultrashort laser pulses, such as those produced by a FS laser, in vivo to produce channels in the TM to relieve glaucoma has not been demonstrated by the work discussed above and presents challenges not present in those experimental studies. In particular, the laser beam must be delivered to a precise location on the TM in such a way as to avoid damage to adjacent and intervening tissue. The challenges of delivering adequate photodisruptive energy in precise patterns in shapes and depths include (a) the curved surface of the target, (b) the target lies beyond the critical angle of visible ocular structures seen through the cornea unaided, (c) optical coupling systems are necessary to visualize and target the intended treatment sites, e.g. trabecular meshwork and Schlemm's canal, (d) the location of Schlemm's canal may be difficult to establish particularly as it lies behind the optically significant trabecular meshwork, (e) once the inner wall of Schlemm's canal therefore the "blood aqueous bather", is penetrated, blood components may obscure the optical pathway for any future optical viewing and/or treating beams.

SUMMARY OF THE INVENTION

The present disclosure provides for the delivery of photodisruptive fluence levels of visible or infrared photons to the precise point of the target tissue of the eye by direct or fiberoptic delivery systems without impinging upon the overlying or surrounding tissue or upon the tissue at the region of beam entry into the eye for the purpose of effecting removal of select tissue in precise shapes and depths. Ultrashort laser pulses are directed into the eye either through the cornea or ab internally via fibers to enable laser radiation, including visible and infrared radiation, under gonioscopic control or through fiberoptic elements, including fiber lasers, thereby effecting precisely controlled photodisruptive removal of such target tissue of the corneo scleral angle. Such tissue may include TM, juxtacanalicular TM, and portions of Schlemm's canal, collector channels, aqueous veins and sclera. Preferably, a laser with pulse duration in the range from 20 fs to 300 ps is used, although it is to be recognized that even shorter pulse durations may be used. The laser uses an optical coupling to affect controlled photodisruption of the target.

It is to be understood that this summary is provided as a means for generally determining what follows in the drawings and detailed description and is not intended to limit the scope of the invention. The foregoing and other objects, features and advantages of the invention will be readily understood upon consideration of the following detailed description taken in conjunction with the accompanying drawings.

BRIEF DESCRIPTION OF THE DRAWINGS

The foregoing summary of this disclosure as well as the following detailed descriptions of the embodiments is further understood when read in conjunction with the accompanying drawings, which are included by way of example, and not by way of limitation with regard to this disclosure.

DETAILED DESCRIPTION

Figure 1:
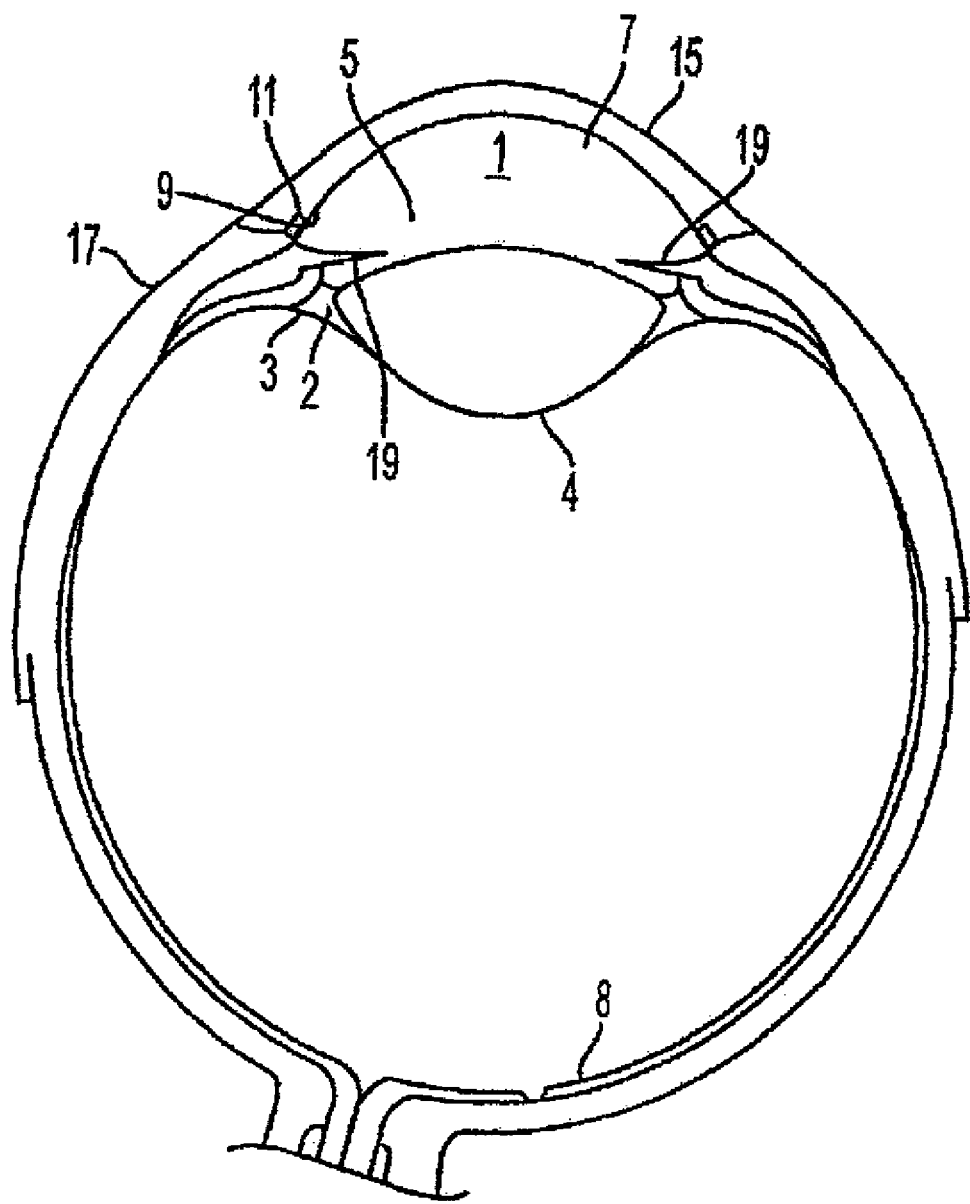
FIG. 1 is a schematic sectional view of an eye illustrating the interior anatomical structure.
Figure 2:
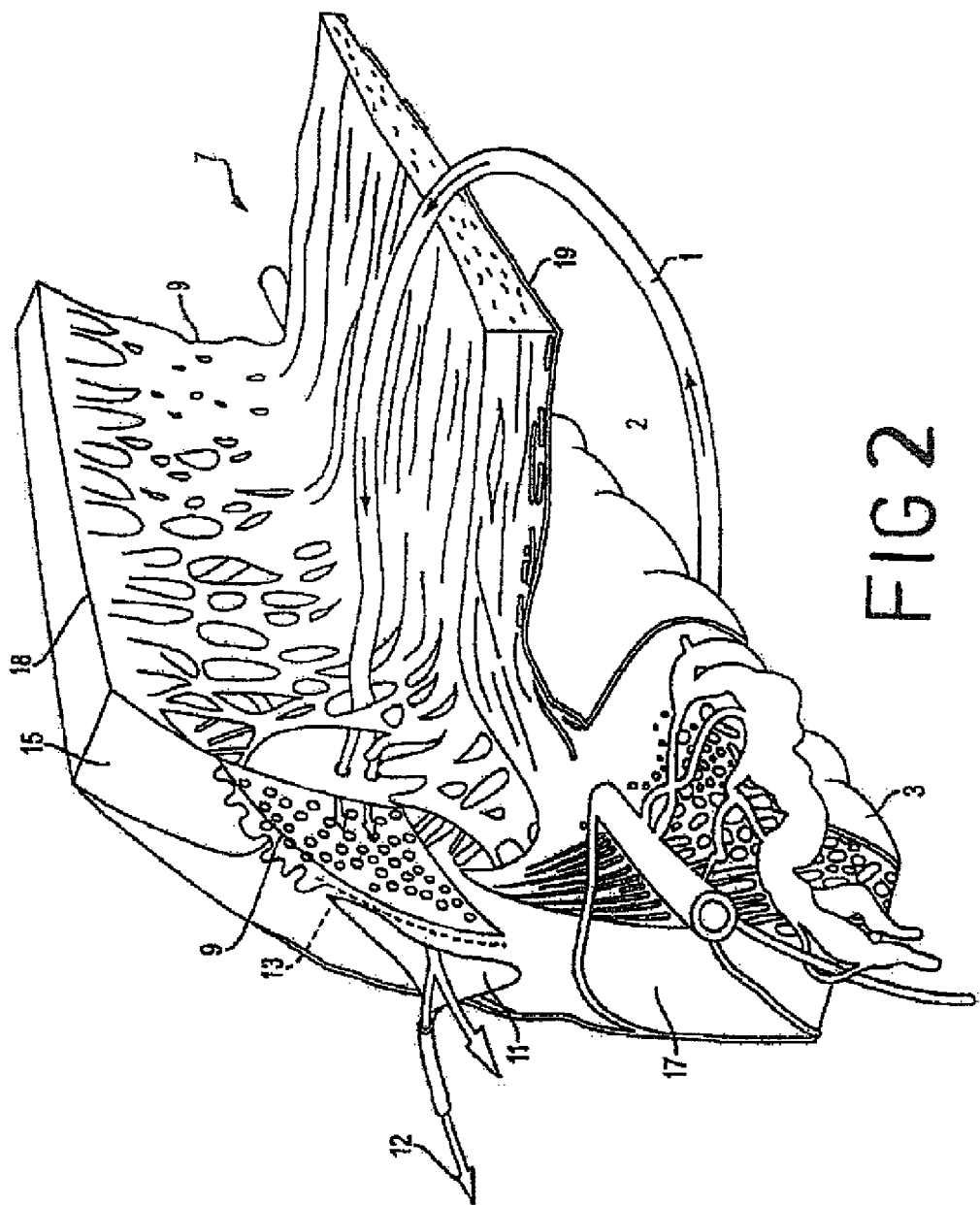
FIG. 2 is a perspective fragmentary view of the anatomy within the anterior chamber of an eye, depicting the corneoscleral angle.

The present disclosure provides for the delivery of photodisruptive fluence levels of visible or infrared photons to the precise point of the target tissue of the eye by direct or fiberoptic delivery systems without impinging upon the overlying or surrounding tissue or upon the tissue at the region of beam entry into the eye for the purpose of effecting removal of select tissue in precise shapes and depths. Ultrashort laser pulses are directed into the eye either through the cornea or ab internally via fibers to enable laser radiation, including visible and infrared radiation, under gonioscopic control or through fiberoptic elements, including fiber lasers, thereby effecting precisely controlled photodisruptive removal of such target tissue of the corneo scleral angle. Such tissue may include TM, juxtacanalicular TM, and portions of Schlemm's canal, collector channels, aqueous veins and sclera. Preferably, a laser with pulse duration in the range from 20 fs to 300 ps is used, although it is to be recognized that even shorter pulse durations may be used. The laser uses an optical coupling to affect controlled photodisruption of the target.

A coupling system employs a goniolens or an ab interno fiberoptic that precisely targets the outflow obstructing tissues to effect removal of the outflow obstruction. Such targeting may include localization of Schlemm's canal, detected optically or otherwise, such as by OCT (optical coherence tomography) or photoaccoustic spectroscopy.

The optical system may also include features to enhance visualization of Schlemm's canal by controlling localized and diffuse pressure gradients, for example by creating relative hypotomy to induce blood reflux into Schlemm's canal. Means of coupling the globe of the eye optically to the laser beam delivery system may be included to enable the exquisite precision of the photodisruptive laser. Such systems include goniolens flange systems, including coupling capabilities such as suction, with diameters in the range of IO to 25 mm, fluidic chambers both to control intraocular pressure ("IOP") and to maintain corneal clarity and shape. To enable optical pathways, such as planar surface to enable precision targeting, suction means for similar purposes which, in addition, exquisitely control light energy delivery registration to the target tissues. In the case of the fiber laser, the fiber may have multiple channels to control intraocular pressure, to enable visualization and optical coupling to Schlemm's canal.

Preferably, the procedure for creating openings in the trabecular meshwork comprises:

(1) imaging the target tissue, (2) locking a pattern to the image, (3) creating the pattern and controlling the depth of laser penetration, and (4) maintaining IOP to enable visualization of Schlemm's canal and concurrently controlling egress of blood to prevent optical decoupling of light obstruction for subsequent laser delivery to target tissue.

Several 20 to 200 µm partial depth openings may be created concurrently without complete penetration to prevent blood reflux or other optical pathway obscuring elements after which Schlemm's canal inner wall penetration is effected to all sites concurrently.

IOP is altered to affect this optical pathway, which is lowered to allow targeting of Schlemm's canal then elevated to prevent blood reflux.

Gonioscopic an fiberoptic delivery systems for laser surgery in the eye wherein thermal and/or radiation damage to the eye is minimized are disclosed.

In connection with glaucoma treatment, laser energy is applied gonioscopicay transcorneal or directed through the fiberoptic element. When gonioscopic, the deflecting mirror may be stationary or may have elements to adjust the mirror within the goniolens delivery system both to precisely target the subject tissue and to precisely direct femtosecond laser energy to these tissues. Such a mirror may be mechanically controllable to effect scanning. The gonioscope is coupled to the eye by various means, including prongs, clips, suction, viscoelastic, aqueous solution and inflatable balloons. The laser delivery system is also coupled both to the goniolens and via the goniolens to the target cornea-scleral angle tissues. The optical delivery is stabilized through precise control of the goniolens and goniolens mirror position and control of the femtosecond laser energy delivered to the target tissue by sensors which detect precise laser tissue interactions as they occur.

The systems may include image stabilization to enable precise laser coupling to the docked goniolens device which includes a mirroring/light deflecting system to enable viewing and treating the cameo scleral angle structure at the laser delivery system, at the goniolens or fiber or both.

In one embodiment a goniolens is applied to the cornea and a laser beam is focused on the target tissue. In another embodiment, a fiberoptic handpiece is passed through an incision in the eye where it is stabilized and secured to the globe and the laser beam is focused on the target tissue.

In one goniolens configuration, a multidimensional mobile reflective surface (e.g., a Mylar balloon) is moved (horizontally, vertical and in depth) by inflation or deflation. This system can include fluidics to control temperature within the lens system. This configuration also may include concurrent illuminating beams and treatment beams with image capture for pixel to pixel image matching to control precise targeting when coupled to a mobile or curved target.

In another goniolens configuration DLP (Digital Light Processing) optical semiconductors or equivalent are used to control the gonioscopic delivery.

In yet another configuration, the system is capable of detecting cardiac cycle pulsation and the filling and emptying causing choroid translation of outflow structures by optical or ultrasound techniques, coupling the detection system to the optical delivery system to enable precise photo disruption of target tissue by means of a combination or individually: (a) mechanically controlled mirror, (b) piezoelectric controlled mirror, (c) DLP optical semiconductor, (d) surface reflecting fluid balloons (e.g. Mylar) included at the laser and/or within a gonioscopic delivery system.

The goniolens air/surface optics are either plano or concave or convex. The mirror/light reflecting element optics are either plano, concave, convex, complex curved or in a segmented mirror array. Light altering materials include variable optical density fluid lair filled balloons, glass, plastic or metal shaped to enable photodisruption to occur at target regions which are both beyond the critical angle to the corneal surface and are curved, residing on the inner surface of a globe.

The laser beam emitted from the laser source may be parallel, convergent or divergent and it is altered by the lens mirror system to enable all forms of emitted beams to focus with a suprathreshold photodisruptive fluence at the target tissue.

In one configuration, the goniolens includes a pressure detection means to compensate for cardiac cycle translation of the entire globe/orbit structures/choroid and intraocular structures including detection of choroidal filling and emptying from cardiac cycle events, which may include pressure detectors in the goniolens or goniolens flange and software in the laser delivery system to compensate for this target translation to enable precise target photodisruption on the moving target.

A concentric ring system may be used to enable (1) registration either through suction or through a retaining mechanical device (prongs, corkscrew) (2) IOP control (3) ocular pulsation detection.

A bladder/balloon system may be used to control optical surfaces, including cornea and any internal mirroring surfaces to enable an emitter to best couple to the target tissue. In coupling the cornea, the cornea may be compressed (e.g. flattened) or the goniolens corneal surface may be curved and coupled to the corneal surface by optically neutral fluidic means, liquids and gels.

In the case of a direct (e.g. non mirror) goniolens delivery system the direct goniolens is retained in a holding device coupled to an optic delivery system with mirror external to the goniolens. Such external mirroring enables the laser source and viewing optics to be inclined at angles from 10° to 170°, often 60° to 120° and most often 80° to 110° in relation to the target tissue.

In the moving eye/goniolens complex the laser fires only when the target is optically captured and stabilized. These optical coupling mechanisms enable precise photodisruption at the target tissue in space and in depth.

In the case of an ab interno fiber, the optical delivery is stabilized through precise control of the fiber position and control of the femtosecond laser energy delivered from the fiber tip by sensors which detect precise fiber tip position and alignment to the target tissue.

The photodisruptive radiation is directed to the target tissues, namely corneoscleral angle structures comprising trabecular meshwork, juxtacanalicular trabecular meshwork, components of Schlemm's canal, and in some cases adjacent cornea, sclera, and iris structures to create fluid passageways between the anterior chamber of the eye and Schlemm's canal or alternatively the suprascleral/subTenon space or alternatively the suprachoroidal space.

Photodisruptive laser energy is targeted to gonioscleral angle structures for the purpose of removing tissue which impedes aqueous outflow or to redirect outflow. Openings are created by patterns of adjacent photodisruption regions in this tissue. The patterns consist of various shapes in size ranging from surface dimensions of 20 to 200 microns and depth adequate to penetrate the inner wall of Schlemm's canal. Patterning enables openings to be created individually, sequentially or several concurrently. In one iteration, when concurrently, the depth is controlled at each opening to allow the creation of craters without entering SC until all craters are at a depth after which minimal additional tissue removal would enter SC thus enabling the optical pathway in the anterior chamber to remain clear. Only at this time would SC be perforated at each crater concurrently to minimize optical pathway obscuration by blood reflux from SC.

In other iterations, in which the IOP is regulated to prevent blood reflux from SC, other patterning options are used, to create individual openings or several concurrent openings in from 1 to 12 clock hours of the angle.

Surgical trauma to the outer wall of Schlemm's canal, or in the case of full thickness penetration to the overlying conjunctiva! and Tenon's tissue, all extremely subject to scarring, is thereby minimized. This is in contrast to current procedures which result in more scarring of sensitive ocular structures and therefore more rapid failure of procedures whose purpose is to control IOP.

By minimizing trauma while creating an aqueous humor egress route, the present invention minimizes healing and increases longevity of improved outflow at the site of filtration. The present invention enables a significantly greater opportunity for success, including the ability to titrate the amount of photodisruptive energy necessary to result in a measured lowering of intraocular pressure.

Figure 6:
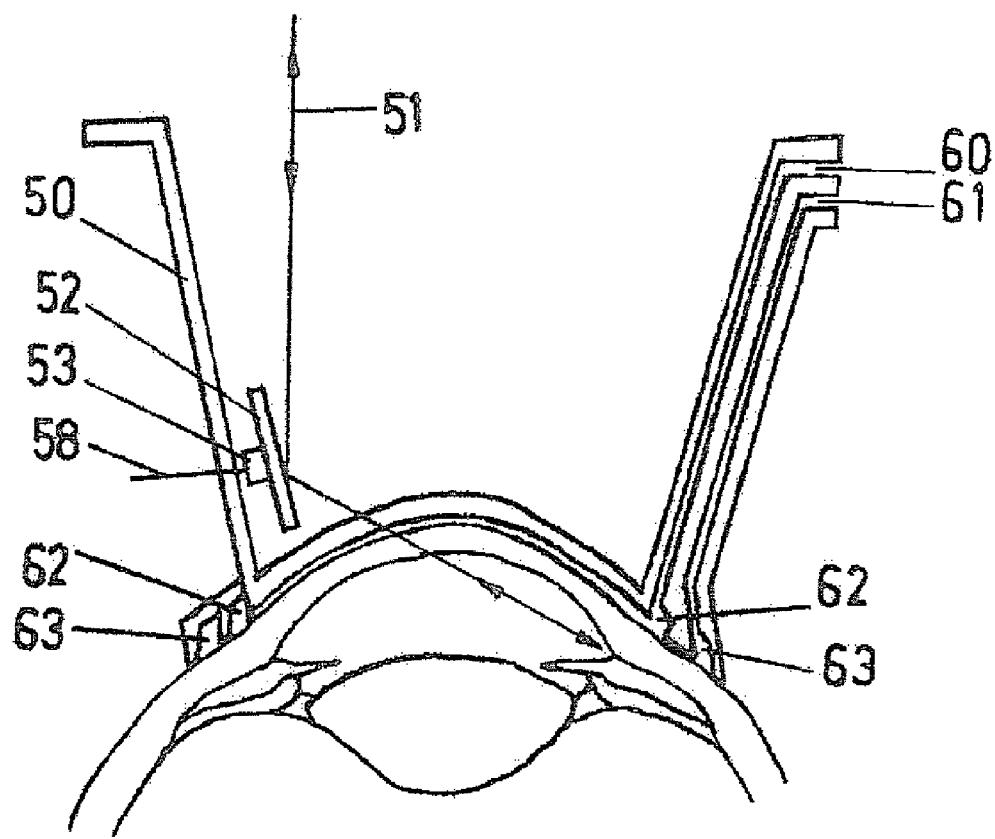
FIG. 6 is a schematic sectional view of an eye with an attached indirect goniolens with an interior mirror. The goniolens is attached to the sclera via suction or mechanical devices.

Referring to FIG. 6, an overview of a method of operating a fiber-optic laser delivery system for treatment of glaucoma or other eye conditions follows: FIG. 6 is a side sectional view of the interior anatomy of a human eye showing fiber-optic probe 23 in relation to an embodiment of a method of treating glaucoma. After applying local and/or peri retrobular anesthesia, a small self-sealing incision 14 can be created in the cornea 15 with a surgical blade or femtosecond laser or other device. The anterior chamber can be further stabilized with a viscoelastic agent. Fiber optic probe 23 can then be positioned and advanced in the incision. 14 into the anterior chamber 7 to target the trabecular meshwork immediately or ab interno or a distal end of fiber-optic probe 23 contacts or is substantially adjacent to the target tissue for removal. Fiber optic probe 23 may be manually directed or held rigid in relation to the ocular structures via anchoring to the globe, sclera 17 or cornea 15 through devices which may include prongs 56 which also may hold in place a pressure regulating system 55 and an ocular pulse sensing system 54.

Laser energy is delivered from the distal end of fiber-optic probe 23 targeting the trabecular meshwork across the anterior chamber or in contact or adjacent to the tissues sufficient to cause photodisruption. Tissues to be removed include the trabecular meshwork 9, the juxtacanalicular trabecular meshwork 13 and an inner wall of Schlemm's canal 11. Fiber-optic probe 23 delivered photodisruptive energy creates an aperture in the proximal inner wall of Schlemm's canal 11 but does not perforate the distal outer wall. In some embodiments, additional apertures can be created in the trabecular meshwork and the target tissue following reposition of the probe. Thus by removing outflow obstructing tissues, the resultant aperture or apertures are effective to restore relatively normal rates of drainage of aqueous humor.

Figure 3:
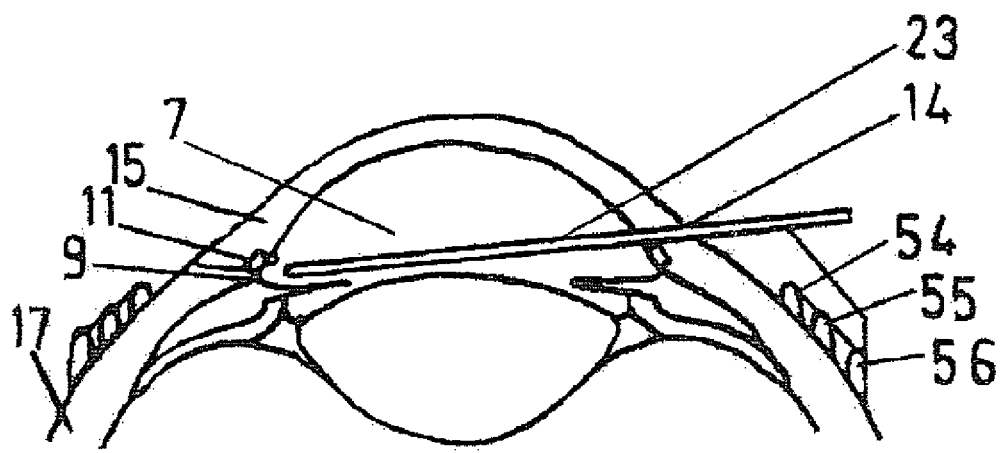
FIG. 3 is a schematic sectional view of an eye illustrating a fiber-optic probe disposed next to the trabecular meshwork in the anterior chamber of the eye.
Figure 4:
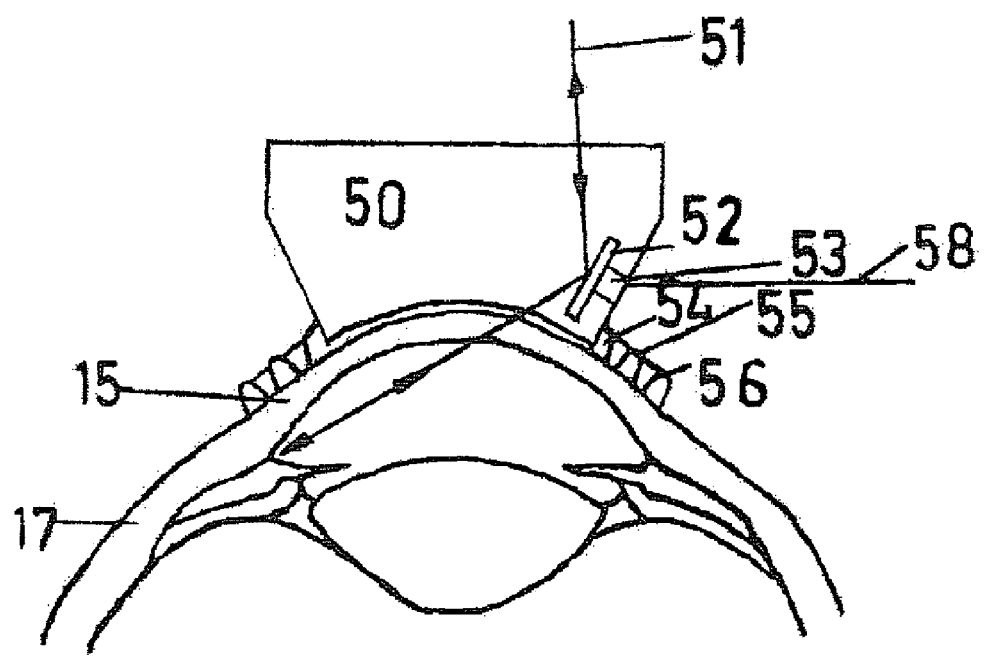
FIG. 4 is a schematic sectional view of an eye with an attached indirect goniolens with an interior mirror. The goniolens is attached to the cornea via suction or mechanical devices.
Figure 5:
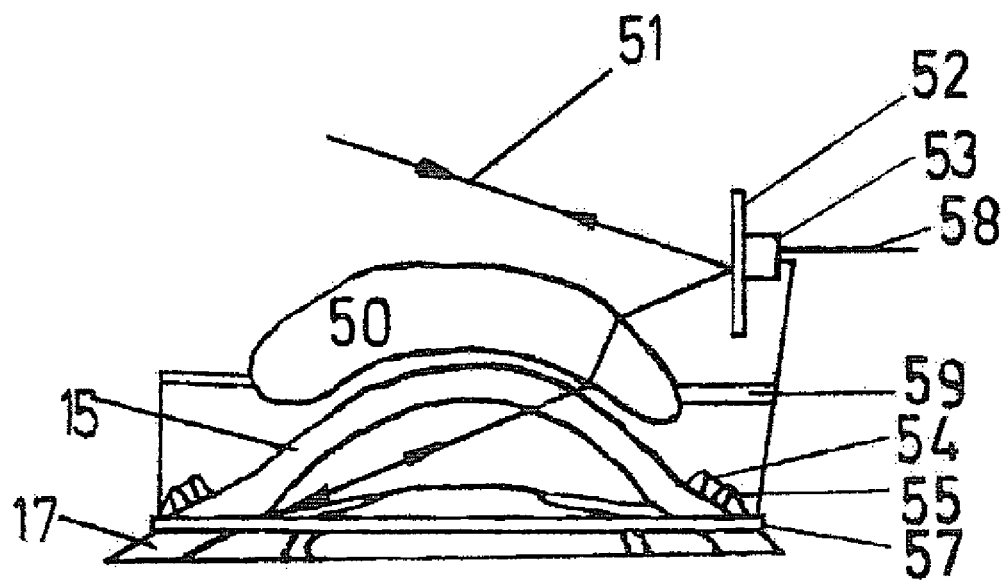
FIG. 5 is a schematic sectional view of an eye with an attached direct goniolens with an external mirror system. The mirror and lens are attached via retaining systems to the sclera.

Referring to FIGS. 3-5, an overview of a method of surgical gonioscopic delivery systems for the treatment of glaucoma or other eye conditions follows: FIG. 3 shows an optical delivery system consisting of an indirect goniolens 50 attached to the sclera 17 mechanically or by prongs 56 or suction, with an internal mirror 52. The mirror may be individual or segmented and fixed or mobile to enable scanning for both viewing and for treatment targeting. In the condition of a mobile mirror/mirror surface, the mirror 52 can be controlled mechanically or pneumatically or with a Mylar type surface reflecting balloon. The mirror can be plano, concave, convex and singular or in a segmented array.

A beam 51 of pulsed radiation is generated by a femtosecond laser and delivered into the eye by the delivery system, including the goniolens 50. The beam 51 is reflected by a mirror 52 which may be controlled by a servo system 53 connected to a controller 58 to focus scanning photodisruptive energy onto the curved surface of the target tissue. The optics enable bidirectional use, one direction is used to treat the target tissue, the other direction is used to view and/or sense the x, y, z coordinates of the targeted tissue to enable precise treatment and removal of the target regions. The beam 51 has a set of pulse parameter ranges specifically selected to photodisrupt targeted tissue of the trabecular meshwork, while minimizing damage to surrounding tissue. Thus, the beam has a wavelength between 0.4 and 2.5 microns. The exact wavelength used for a particular subject depends on tradeoffs between strong absorption by the meshwork and transmission of preceding ocular structures and aqueous humor. FIG. 4 shows an indirect goniolens 50 attached to the cornea 15 mechanically 56 or by suction with an internal mirror 52. FIG. 5 shows a direct goniolens attached to the sclera 17 by suction 57 or mechanically with a mirror system 52 external to the goniolens.

The pulse duration of the laser beam is chosen to have a high probability of photodisrupting material of the corneoscleral angle outflow tissues. There is an inverse relationship between the laser pulse duration and the energy required in each pulse to generate optical breakdown. The pulse duration is selected to be shorter than the thermal relaxation of the target so that only the targeted material is heated, and the surrounding tissue is unaffected. Thus, the pulse duration is between 20 fs and 300 ps. The pulse rate is between 1 and 500 KHz.

The pulse energy is chosen to facilitate photodisruption and minimize the shockwave effect of the laser light. A typical value for the pulse energy is between 300 to 1500 nJ.

The spot diameter is chosen such that sufficient laser energy density is provided to facilitate photodisruption of the trabecular meshwork tissue. The spot size is between 1 to 10 microns.

The goniolens 50 is anchored either on the sclera 17 or the cornea 15 by a suction ring 57 or prongs 56. The anchoring system is attached to a pressure regulating system 55 and an ocular pulse sensing system 54. The anchoring system is either concentric 57 or segmented 56. Scanning the spot in the x, y, and z direction effects patterns for tissue removal.

Figure 7:
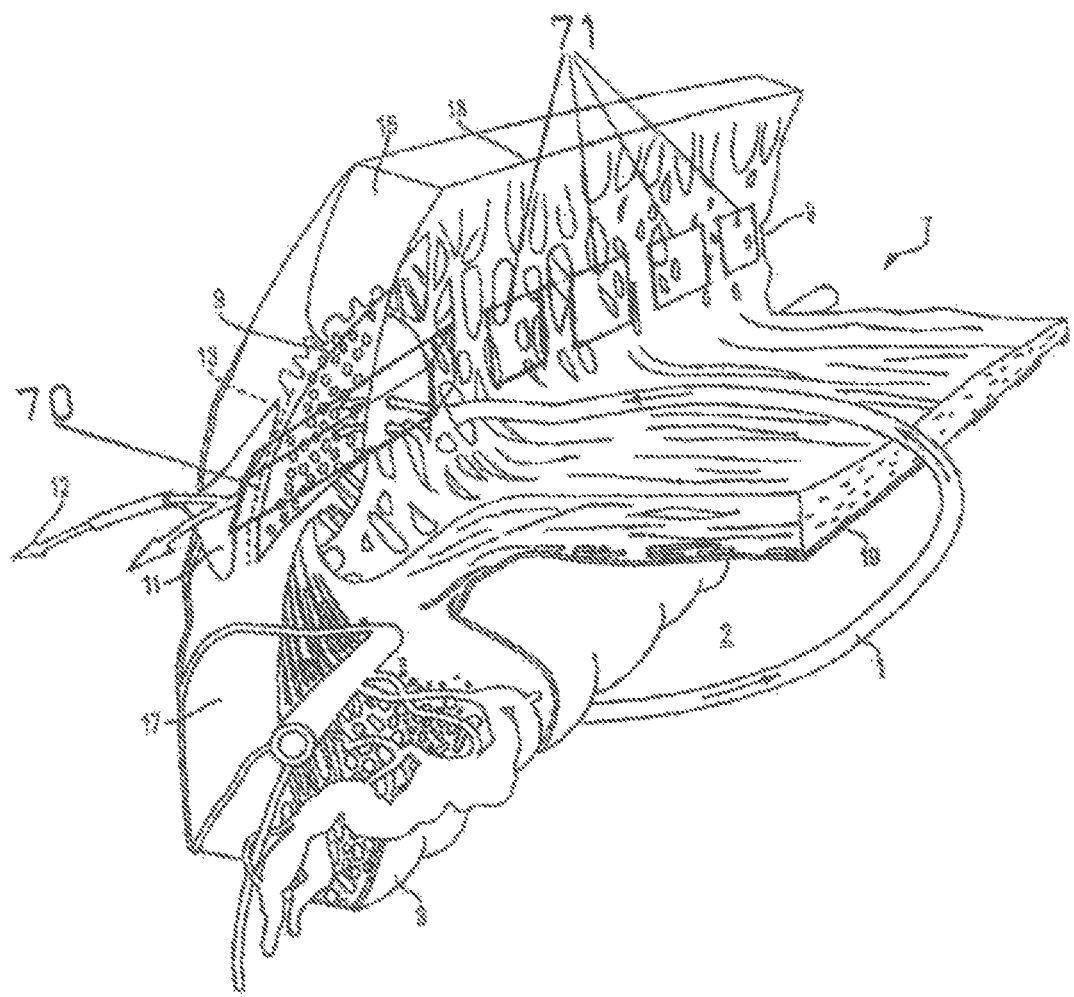
FIG. 7 is a fragmentary cross section of the anatomy within the anterior chamber of an eye, showing a segment of target tissue to be photodisrupted.

FIG. 7 shows the target tissue to be photodisrupted in a perspective view 70 and in a cross-sectional view 71. In this case a single site is demonstrated but understood is duplication of this site over several regions individually or concurrently.

Alternatively, the TM may be approached ab externo via the semi-transparent sclera using high numerical aperture optics and a fundamental wavelength that allows deep penetration through the sclera. This produces targeted ablation of the deep corneo scleral angle structures, specifically targeting TM, JCTM and portions of Schlemm's Canal. In this instance the coupling lens could be planar or curved.

All coupling lenses, goniolenses and fibers require focusing devices at the laser which couple optically to the lenses, goniolenses and fibers to effect appropriate fluences at the target tissue to effect micro ablations and thereby tissue removal.

Preferably, the procedure for ultrashort laser pulse trabeculostomy comprises the steps that follow.
1. Prepare patient for femto laser trabeculostomy procedure.
2. Prepare femto laser which has been pretested on a model of trabecular meshwork for accuracy and fluence at the target tissue.
3. Align gonio lens with optical alignment system of laser visualization system to target planned trabecular meshwork tissue sites and lock the target into the system for treatment.
4. In the case where the gonio lens mirror is not stationary, but mobile, assure the tracking system is engaged to control all optical surfaces.
5. Secure the gonio lens onto the eye. This may be pneumatic or physical engagement to control all movement and enable tracking system to engage and apply energy only when target is precisely focused for appropriate delivery of laser energy to the target sites. If mobile, laser will only engage when precise target alignment assures exact tissue targeting in x, y and z loci.
6. Anchor the gonio lens either on the cornea or the sclera either by prongs or a suction ring.
7. Attach anchoring system to a pressure regulating system and an ocular pulse sensing system.
8. In the case where cardiac cyclic translation of target is monitored and controlled, engage this system to enable precise depth targeting.
9. Couple end of optical pathway to a fem to second laser.
10. Locate Schlemm's canal with the gonioscope.
11. The goniolens mirror may be curved to allow targeting of curved trabecular meshwork.
12. Focus laser beam on target tissue.
13. Photodisrupt target tissue until crater forms adjacent to Schlemm's canal.
14. Repeat step 14. up to 10 times in a pattern, for example, from 5 o'clock to 1 o'clock.
15. The patterns consist of various shapes in size ranging from surface dimensions of 20 to 200 microns and depth adequate to penetrate the inner wall of Schlemm's canal.
16. Using the laser, concurrently extend craters so they become ostia into Schlemm's canal.
17. Detach gonioscope.
18. In the case where femto laser energy is delivered fiberoptically within the eye, all above apply. In addition, following paracentesis and stabilization of the anterior chamber with aqueous and/or viscoelastic agents, the fiberoptic delivery system is placed into the anterior chamber and imaging of all relevant structures is performed to assure targeting to planned sites. The fiber and fiber position maintaining devices are engaged and enabled, manually and/or automatically.

The terms and expressions which have been employed in the foregoing specification are used therein as terms of description and not of limitation, and there is no intention, in the use of such terms and expressions, to exclude equivalents of the features shown and described or portions thereof, it being recognized that the scope of the invention is defined and limited only by the claims that follow.

What is claimed is:

1. A method of creating one or more channels in a trabecular meshwork of an eye of a patient to conduct fluid from an anterior chamber into a Schlemm's canal of the eye, comprising:
   ablating a first region to a first depth in one or more of the trabecular meshwork or the Schlemm's canal with first laser pulses;
   ablating a second region to a second depth in the one or more of the trabecular meshwork or the Schlemm's canal with second laser pulses; and
   extending the first region with third laser pulses to a third depth and extending the second region with fourth laser pulses to a fourth depth, so as to form the one or more channels along the trabecular meshwork and into the Schlemm's Canal to conduct fluid from the anterior chamber into the Schlemm's canal;
   wherein each of the laser pulses comprises a wavelength of within a range from 0.4 to 2.5 microns, a fluence level to produce optical breakdown, and a pulse duration in a range from 20 femtoseconds to 300 picoseconds.

2. The method of claim 1, wherein the laser pulses are directed through a cornea of the eye to ablate the trabecular meshwork.

3. The method of claim 1, wherein a gonioscopic lens is coupled to the eye and the laser pulses are transmitted through the gonioscopic lens.

4. The method of claim 1, wherein the laser pulses are scanned in an ablation pattern comprising adjacent regions in the trabecular meshwork to form the one or more channels.

5. The method of claim 1, wherein the laser pulses are reflected off a curved mirror and wherein the laser pulses are scanned and focused into a curved trabecular meshwork to form the one or more channels in the curved trabecular meshwork.

6. The method of claim 1, wherein an intraocular pressure of the eye is lowered to allow targeting of the Schlemm's canal and then elevated to prevent blood reflux.

7. The method of claim 1, wherein the Schlemm's canal is detected optically or by optical coherence tomography (OCT) or by photoacoustic spectroscopy.

8. The method of claim 1, wherein the laser pulses are directed through a sclera of the eye to ablate the trabecular meshwork.

9. The method of claim 1, wherein at least a portion of the trabecular meshwork comprises a lattice structure having voids, and the channel results in fluid communication between the Schlemm's Canal and one or more of the voids.

\* \* \* \* \*